United States Patent
Thiele et al.

(10) Patent No.: US 9,585,567 B2
(45) Date of Patent: Mar. 7, 2017

(54) METHOD TO COMPUTE AND PRESENT BRAIN AMYLOID IN GRAY MATTER

(71) Applicant: KONINKLIJKE PHILIPS N.V., Eindhoven (NL)

(72) Inventors: Frank Olaf Thiele, Aachen (DE); Fabian Wenzel, Hamburg (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 30 days.

(21) Appl. No.: 14/355,599

(22) PCT Filed: Nov. 13, 2012

(86) PCT No.: PCT/IB2012/056379
§ 371 (c)(1),
(2) Date: May 1, 2014

(87) PCT Pub. No.: WO2013/072843
PCT Pub. Date: May 23, 2013

(65) Prior Publication Data
US 2014/0257084 A1 Sep. 11, 2014

Related U.S. Application Data

(60) Provisional application No. 61/560,319, filed on Nov. 16, 2011.

(51) Int. Cl.
*A61B 6/00* (2006.01)
*G01R 33/48* (2006.01)
(Continued)

(52) U.S. Cl.
CPC .......... *A61B 5/0035* (2013.01); *A61B 5/0042* (2013.01); *A61B 5/055* (2013.01);
(Continued)

(58) Field of Classification Search
CPC ..... A61B 5/0035; A61B 5/0042; A61B 5/055; A61B 6/037; A61B 6/466
See application file for complete search history.

(56) References Cited

U.S. PATENT DOCUMENTS 6,819,952 B2 11/2004 Pfefferbaum et al.
8,000,773 B2 * 8/2011 Rousso .................. A61B 5/415
250/370.08
(Continued)

FOREIGN PATENT DOCUMENTS

DE 102007018630 A1 10/2008
WO 2008093057 A1 8/2008
(Continued)

OTHER PUBLICATIONS

Ashburner, J., et al.; Unified segmentation; 2005; NeuroImage; 26:839-851.
(Continued)

*Primary Examiner* — Baisakhi Roy

(57) ABSTRACT

An imaging work station (20) includes one or more processors programmed to receive (170) an image depicting a distribution of a radiotracer in a brain or other region of interest. The radiotracer includes at least one of [18F]-Flutemetamol, [18F]-Florbetaben, and [18F]-Florbetapir which highlights amyloid deposits. The image and a template or an MRI image of the region of interest which includes a segmented anatomical feature, such as gray matter, are registered (180) to a common space. A volume representation of the image which depicts the distribution of the radiotracer in the segmented gray matter and suppresses the radiotracer outside of the segmented anatomical feature in white matter is extracted (210).

16 Claims, 3 Drawing Sheets

Figure 1:
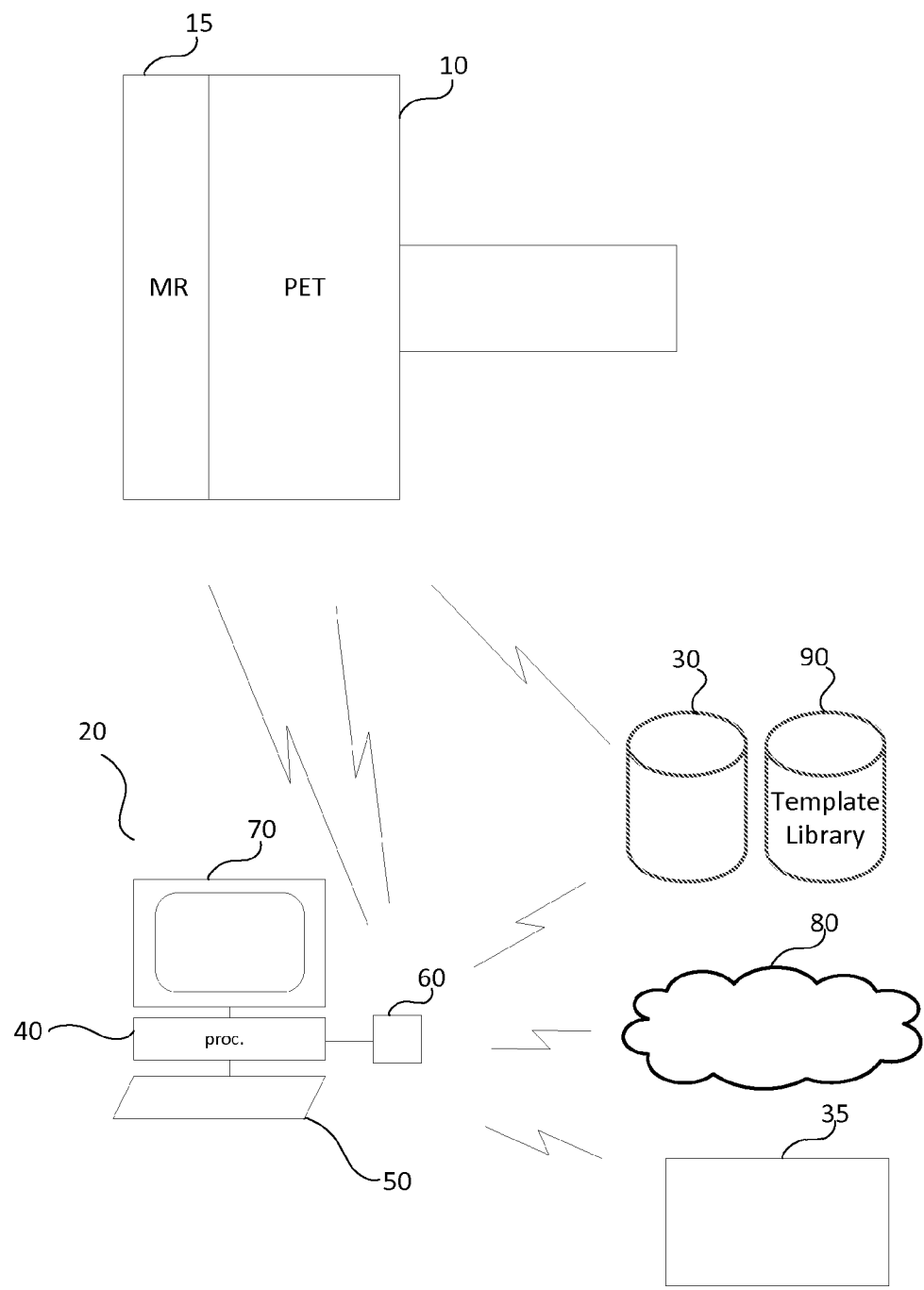

(51) Int. Cl.
*A61B 5/055* (2006.01)
*A61B 5/00* (2006.01)
*A61B 6/03* (2006.01)
*G06T 7/00* (2006.01)

(52) U.S. Cl.
CPC .............. *A61B 6/037* (2013.01); *A61B 6/501* (2013.01); *A61B 6/5247* (2013.01); *G01R 33/481* (2013.01); *G06T 7/0012* (2013.01); *G06T 7/0014* (2013.01); *A61B 6/466* (2013.01); *G06T 2207/10088* (2013.01); *G06T 2207/10104* (2013.01); *G06T 2207/30016* (2013.01)

(56) References Cited

U.S. PATENT DOCUMENTS

| | | | |
|---|---|---|---|
| 9,002,081 B2* | 4/2015 | Brown | G06T 7/0014 382/128 |
| 2007/0081707 A1* | 4/2007 | Sirohey | G06F 19/3431 382/128 |
| 2008/0267870 A1* | 10/2008 | Gerdes | C07D 401/04 424/1.85 |
| 2009/0030304 A1 | 1/2009 | Feiweier et al. | |
| 2009/0252391 A1* | 10/2009 | Matsuda | A61B 5/055 382/131 |
| 2009/0274624 A1* | 11/2009 | Pike | A61K 51/0455 424/1.89 |
| 2010/0055036 A1 | 3/2010 | Suhara et al. | |
| 2010/0080432 A1 | 4/2010 | Lilja et al. | |
| 2010/0135556 A1* | 6/2010 | Razifar | G06T 7/0083 382/131 |
| 2011/0160543 A1* | 6/2011 | Parsey | A61B 5/055 600/300 |
| 2011/0257407 A1* | 10/2011 | Klunk | A61K 31/428 548/178 |
| 2013/0266513 A1* | 10/2013 | Johnson | A61K 51/04 424/1.89 |
| 2013/0336564 A1* | 12/2013 | Hu | G01R 33/481 382/131 |

FOREIGN PATENT DOCUMENTS

| | | |
|---|---|---|
| WO | 2010095065 A1 | 8/2010 |
| WO | 2010119388 A1 | 10/2010 |
| WO | 2011/044406 | 4/2011 |
| WO | 2011106732 A1 | 9/2011 |

OTHER PUBLICATIONS

Barthel, H., et al.; Individualized quantification of brain B-amyloid burden: results of a proof of mechanism phase 0 florbetaben PET trial in patients with Alzheimer's disease and healthy controls; 2011; European Journal Medical Molecular Imaging; 38:1702-1714.

Minoshima, S., et al.; A Diagnostic Approach in Alzheimer's Disease Using Three-Dimensional Stereotactic Surface Projections of Fluorine-18-FDG PET; 1995; Journal of Nuclear Medicine; 36(7)1238-1248.

Swaminathan, S., et al.; Amyloid pathway-based condidate gene analysis of [11C] PiB-PET in the Alzheimer's Disease Neuroimaging Initiative (ADNI) cohort; 2012; Brain Imaging and Behavior; 6:1-15.

* cited by examiner

METHOD TO COMPUTE AND PRESENT BRAIN AMYLOID IN GRAY MATTER

CROSS REFERENCE TO RELATED APPLICATIONS

This application is a national filing of PCT application Serial No. PCT/IB2012/056379, filed Nov. 13, 2012, published as WO 2013/072843 A1 on May 23, 2013, which claims the benefit of U.S. provisional application Ser. No. 61/560,319 filed Nov. 16, 2011, which is incorporated herein by reference.

The present application relates to the diagnostic imaging arts. It finds particular application in the detection of amyloid deposition and will be described with particular reference thereto.

Amyloid deposition (Aβ) in the brain is one of the hallmarks of Alzheimer's disease. Brain scans are commonly performed using fluorodeoxyglucose (FDG) radiotracers, but FDG radiotracers do not target Aβ. There are new Positron Emission Tomography (PET) radiotracers undergoing phase three clinical trials for use in determining Aβ, e.g. [18F]-Flutemetamol, [18F]-Florbetaben, and [18F]-Florbetapir. One method of Aβ quantification is kinetic modeling of dynamic PET time series with arterial blood sampling. Although this provides good quantification, a clinical use is problematic. More practical alternatives use the comparison of uptake in a reference region in comparison with a target region. The reference region selected, such as the cerebellum, contains predominately gray matter (GM). Static images are taken during an approximate 20 minute period 30-40 minutes after injection of the radiotracer. An average is taken of the standard uptake values (SUV) in the target region and an average is taken of the SUV in the reference region. A ratio of standard uptake values (SUVRs) is obtained by mean($SUV_{target}$)/mean($SUV_{reference}$) SUVRs are used to normalize the intensity of the radiotracer present in the brain image. SUVRs can also be computed and displayed for each image voxel (SUVR image). The reference region represents unspecific binding of the radiotracer. Theoretically, it should exclude white matter, but correct delineation is difficult.

Unlike FDG, which has a very low white matter uptake, these new radiotracers are also taken up by white matter. Gray matter (GM) uptake has diagnostic value concerning Alzeheimer's disease while white matter is attributed to unspecific binding and has minimal diagnostic value.

White matter dominates the brain and brain images showing Aβ with a radiotracer will be dominated by the presence of the radiotracer in white matter areas. While brain scans with little or no uptake and those with large uptake are easily diagnosed, those with intermediate amounts call for quantification methods. Additionally, for images where the uptake is high in both white and gray matter, separation of signals along a projection ray into white matter and gray matter is difficult. The maximum along a projection ray will often be located in white matter and a mean or quantile value will, in general, also not differentiate between gray matter and white matter.

The present application presents a new and improved computation and presentation of amyloid in gray matter that overcomes the above limitations.

In accordance with one aspect, an imaging work station includes one or more processors programmed to receive an image depicting a distribution of a radiotracer in a region of interest. The image is registered to a common space defined by a template or an MRI image of the region of interest which includes a segmented anatomical feature. A volume representation of the image which depicts the distribution of the radiotracer in the segmented anatomical feature and suppresses the radiotracer outside of the segmented anatomical feature is extracted.

In accordance with another aspect, a method for brain imaging, after administration of a radiotracer, receives at least one image depicting a distribution of a radiotracer in a region of interest. With one or more processors, the image is registered to a common space defined by a template or an MRI image of the region of interest which includes a segmented anatomical feature. A volume representation of the image which depicts the distribution of the radiotracer in the segmented anatomical feature and suppresses the radiotracer outside of the segmented anatomical feature is extracted.

In accordance with another aspect, an imaging system includes a PET scanner and an imaging work station. The imaging work station receives a radiotracer brain image from the PET scanner, segments gray matter of the received brain imaging data using at least one of: a template, and a MR brain image, and displays an image of the radioisotope in the gray matter, with a measure of radiotracer concentration shown as intensity.

One benefit of the present application is the suppression of the dominant white matter uptake in the measurement of the radiotracer.

Another benefit is the use of other image information to determine the location of patient GM.

Another benefit is the focus on the brain GM Aβ important in the diagnosis of Alzheimer's disease.

Another benefit is the integration with a Clinical Decision Support systems (CDS) or a Picture Archiving and Communication Systems (PACS).

The invention may take form in various components and arrangements of components, and in various steps and arrangements of steps. The drawings are only for purposes of illustrating the preferred embodiments and are not to be construed as limiting the invention.

FIG. 1 illustrates one embodiment of an imaging system diagrammatically.

Figure 2:
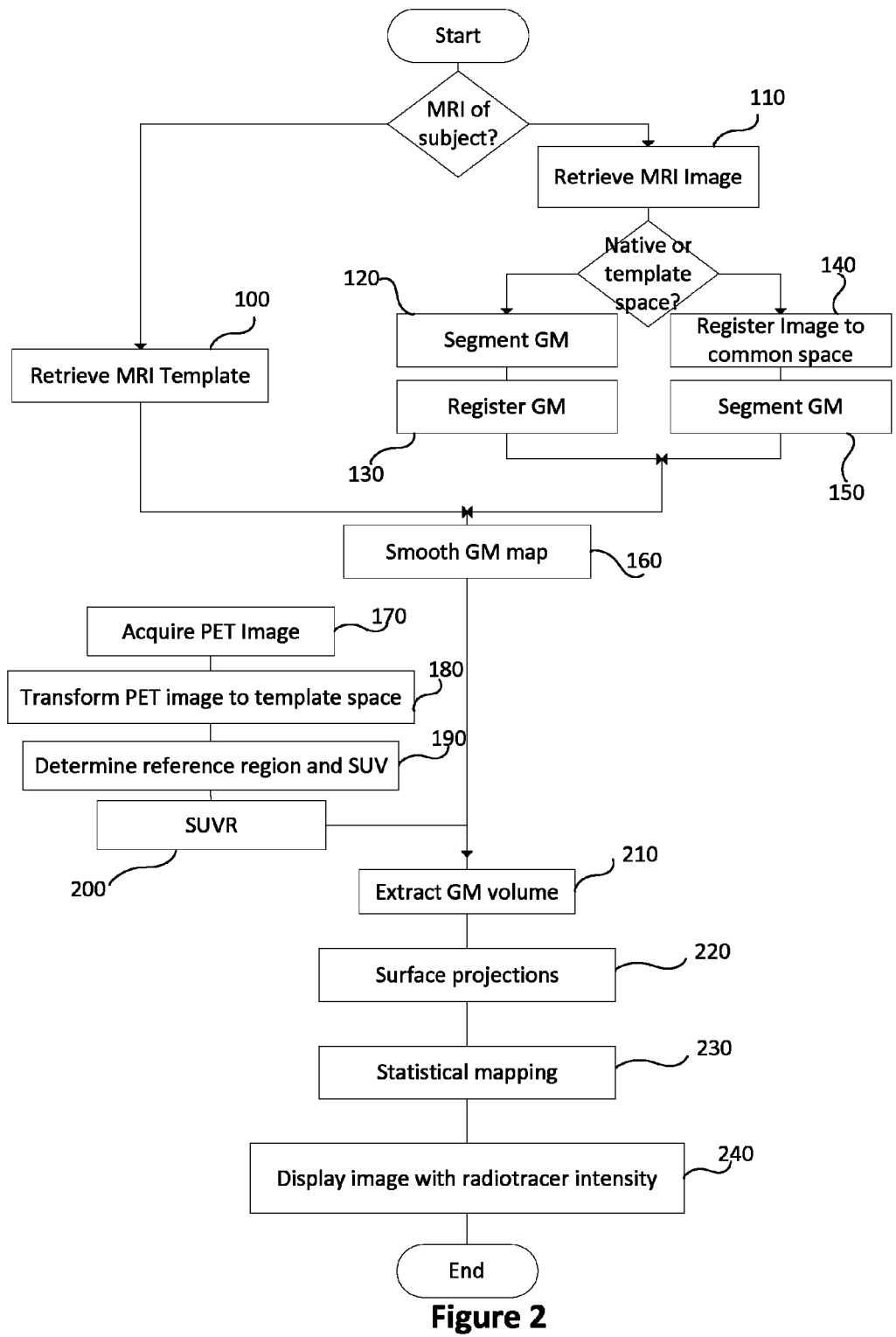

FIG. 2 flowcharts one embodiment of a method for imaging with a radiotracer which suppresses non-diagnostic white matter.

Figure 3:
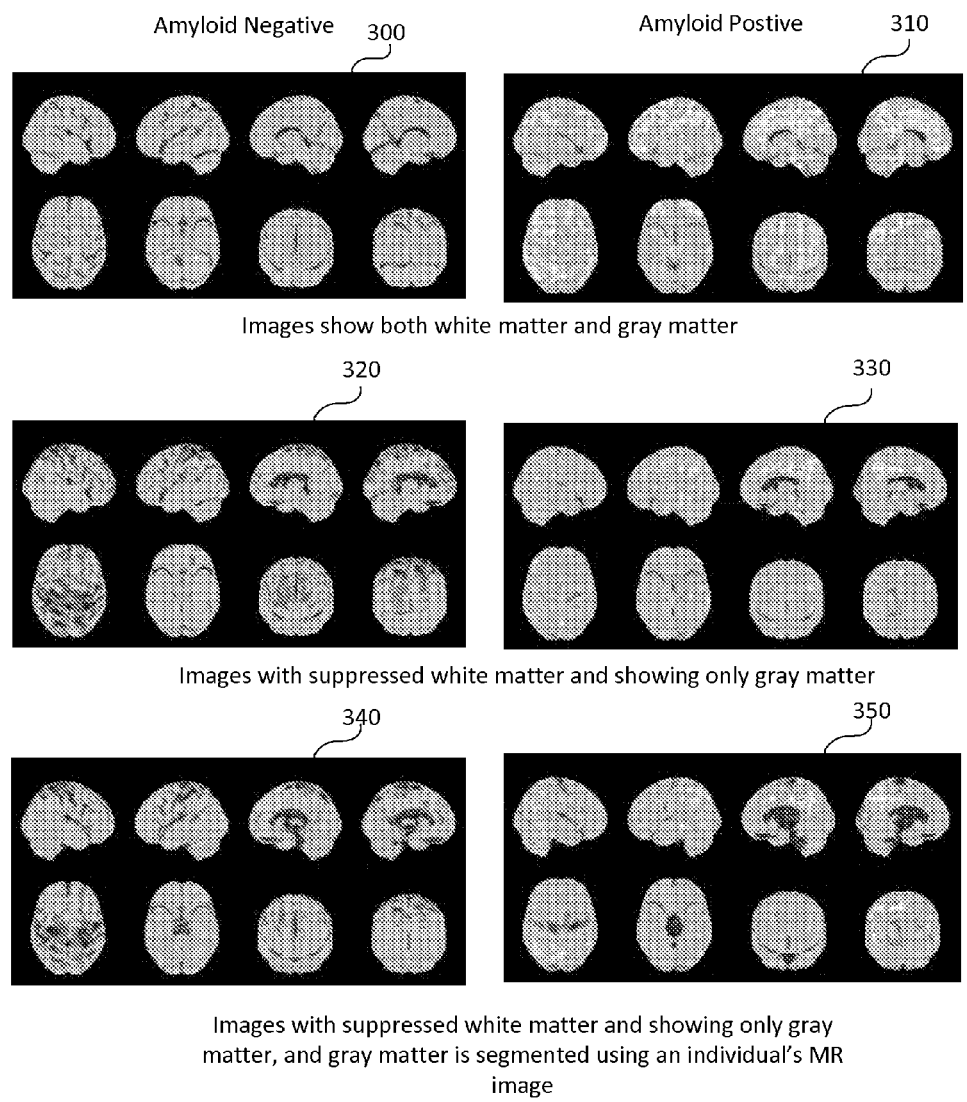

FIG. 3 depicts the difference in imaging in one example of one embodiment.

With reference to FIG. 1, an embodiment of an imaging system is diagrammatically illustrated. The imaging system includes a nuclear scanner 10, such as a PET or SPECT scanner which scans a subject's brain for the presence or uptake of a radiotracer. The scanner records the events which occur due to the radiotracer emissions. The events are recorded in an event list which is communicated to an imaging work station 20 which reconstructs an image depicting a distribution of the radiotracer in the brain. The work station 20 is in communication with the scanner 10 and can be local or remote. The PET scanner in other embodiments can optionally be combined with other scanners that generate images which differentiate between white and gray matter such as a Magnetic Resonance Imaging (MRI) scanner 15. In one embodiment, the nuclear and MR scanners are combined and have a common imaging area such that their images are inherently registered.

The work station 20 receives the imaging data from the PET scanner directly or is stored and then later retrieve from storage memory 30. The work station 20 can operate stand-alone or integrate with systems 35 such as a picture archieve and retrieval system (PACS) or a clinical decision support system (CDS). The workstation includes one or more processors 40 interconnected to an input device 50, a communication device 60, and a display device 70. The input device 50 or devices allow the healthcare practitioner to interact with the system. The work station 20 uses a communication device 60 which allows the work station to communicate with other systems or the Internet 80. The work station can access templates locally or retrieve them from template libraries or repositories 90 which store brain templates. Images and templates can be stored in a local data store or remotely or as part of an integrated system such as the PACS or the CDS. The display device 70 displays images, portions of images, or other parameters and menus.

With reference to FIG. 2, a flowchart illustrates one embodiment of a process performed by the processor 40. A gray matter (GM) map is obtained using one of several of alternatives. One alternative in a step 100 is to use a brain template, such as one that provides a probability that each voxel of the brain is white or gray matter. The templates can be based on a nominal patient, or can be age, gender, size specific or the like. The template can be sized or otherwise adapted to the current patient. The template includes a GM map in template space. Such GM maps are feely available, e.g. the MM-ICBM atlas. The GM maps indicate the probability of the presence of GM in each voxel of the mapped nominal brain.

Another alternative is to generate or retrieve a Magnetic Resonance Imaging (MRI) image of the specific patient in a step 110. The image can be stored and retrieved using the PACS, or retrieved directly from the MRI scanner 15. The GM is segmented in the MRI image in native MRI image space in a step 120. Alternatively, the image is transformed to template space in a step 140, and the GM is segmented in template space in a step 150. Reversing the transforming and segmenting still yields a GM map in template space and the transform which describes the relationship between template and native spaces. Using a unified segmentation approach yields a GM tissue probability map and, optionally, the native MRI image space is transformed into the template space in a step 130. Another method produces a binary GM map.

The GM map in template space can be smoothed in a step 160, e.g. with a Gaussian kernel of approximately 5-10 mm, which allows for residual alignment error in both MRI warping and MR-PET alignment.

A PET or SPECT image is received in a step 170 using the scanner 10. The PET image is acquired after administration of a radiotracer, particularly [18F]-Flutemetamol, [18F]-Florbetaben, [18F]-Florbetapir or another radiotracer specific to Aβ in GM. The Step 170 can be performed concurrently with or after the steps of obtaining a GM map.

Once the PET image is received, the PET image is registered to template space or native MRI image space in a step 180. If the segmentation is from the brain template, the PET image is transformed into template space. If the MRI was used to obtain the segmented GM map in the step 120, then the PET image can be registered to the MRI image in the native MRI image space rather than template space. As another alternative, the PET and MRI images can both be transformed to template space with the transfrom from the step 140.

An intensity normalization is performed using a reference region such as a cerebellum in a step 190. A standardize uptake value (SUV) for a nominal or average voxel of the reference region is calculated. In a step 200, the SUV of each voxel of the PET image is divided by the SUV of the reference region to generate a standardized uptake value ratio (SUVR) for each voxel. The SUVR is used to normalize the intensity of the image voxels.

The GM volume represented by the PET image is extracted in a step 210 using the smoothed GM map from the step 160. The GM volume representation confines the PET image to GM voxels. More specifically, the voxel intensity, I(i) for each voxel i weighted with the probability GM(i) from the smooth GM map that the voxel i is gray matter to suppress the white matter uptake. v(i)=GM(i)×I(i), for each voxel i. In this manner, a volume image is generated in which each voxel in the GM has a value proportional to the normalized uptake of the radioisotope tracer and each voxel in the white matter zeroed or substantially zeroed. This value image can be displayed on the display device 70 in various ways, such as slice images, volume renderings, maximum intensity projection images, and the like.

In one embodiment, in an optional step 220, the voxel values are projected up onto surfaces of the brain. Surface projection rays are created. For each projection ray, a value is computed and projected onto the cortical surface. For each surface pixel, the image voxels along a ray projected normal to the surface pixel are combined. In one example, the pixel value is represented by $f(GM(x \in p_i), I(x \in p_i))$, where $GM(x)$ is the GM presence at voxel x, I(x) is the intensity at voxel x, $p_i$ is the projection ray (image voxels along the normal projection ray) and $f$ is a function that computes a scalar value based on the GM and intensity. For example, when $f=\max_{x \in p_i} GM(x) \times I(x)$ the maximum weighted intensity voxel along the ray is projected to the surface pixel. As another example, when $$f = \frac{1}{z} \sum_{x \in p_i} GM(x) \times I(x)$$

where Z is a normalization factor, e.g., chosen to be unity (Z=1), or normalized for the GM density along the ray, the surface pixel value is a weighted sum or average of the weighted intensities of the voxels along the ray. In a FDG PET, the projection rays are typically a fixed length, such as 13 mm. For use in this technique, greater ray lengths such as 15 mm to 20 mm confined by the GM map and choice of projection function $f$ are contemplated.

In an alternative embodiment, location dependent projection ray lengths are used to improve quantitative accuracy. The location dependent projection rays capture the anatomical variability of the GM thickness across the cortical surfaces.

A statistical mapping is applied to the subject's volume or surface representation in a step 230. A t-value (z-score) is computed for each voxel or pixel, i, where $$t(i) = \frac{v(i) - \mu(i)}{\sigma(i)},$$

where v(i) is the voxel intensity and μ(i) and σ(i) are an estimated mean and standard deviation of voxel i of PET radiotracer images within a group of subjects registered to the common space with well-defined status of radiotracer load such as Aβ-negative brains. Estimation of the mean and standard deviation within such a group are processed consistently and the same as the present subject with regard to intensity normalization and choice of GM map. The statistical mapping provides a comparison of the image with a group of "normal" individuals which results in a probability of the image voxel being different from normal.

The statistically mapped volume or surface representations, the brain surface projections, volume slices or the like are displayed on a display 70 in a step 240. In one instance, the GM Aβ are displayed as images which include only GM with Aβ levels shown using color to represent intensity. The displays includes views such as lateral, medial, superior, inferior, anterior, and posterier perspectives of the volume and/or surface projections.

With reference to FIG. 3, an example depicts the changes in images with suppression of non-diagnostic regions of uptake. Images 300, 320, 340 are Aβ negative brains and images 310, 330, 350 are Aβ positive brains. In the top pair of images 300, 310, both white and GM are shown with the radiotracer. In image 300, the Aβ negative image depicts no Aβ. In image 310, the Aβ dominates the image. In contrast, suppressing the white matter and displaying only GM in image 330, the Aβ represented is considerably reduced. A further enhancement in image 350 results from applying individual GM segmentation (120,130 in FIG. 2). The images 320 and 340 provide comparison of the Aβ-negative images using GM only, and GM only with individual GM segmentation.

The method of segmenting the region of diagnostic value and suppressing other regions with uptake can be applied to other areas of imaging. Suppressing regions which uptake radiotracers, but do not contribute to diagnosis can be applied to any area of the body or the use of any radiotracers. Suppressing the non-diagnostic regions and displaying only the diagnostic valuable regions provides a more accurate diagnosis. The more the non-diagnostic region dominates the volume and uptake, the greater the advantage of suppression.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An imaging work station comprising:
one or more processors programmed to:
    receive an image depicting a distribution of a radiotracer in a region of interest that includes the brain;
    register the image to a common space defined by a template or an MRI image of the region of interest, the common space including a segmented anatomical feature representing a probability that each voxel is gray matter; and
    extract a volume representation of the image which depicts the distribution of the radiotracer in the segmented anatomical feature and suppresses the radiotracer outside of the segmented anatomical feature by combining each voxel of the image with the probability of the voxel being gray matter as represented by the registered common space.

2. The imaging work station according to claim 1, wherein the radiotracer highlights amyloid deposits.

3. The imaging work station according to claim 1, wherein the radiotracer includes at least one of [18F]-Flutemetamol, [18F]-Florbetaben, and [18F]-Florbetapir.

4. The imaging work station according to claim 1, wherein the processor is further programmed to:
    calculate a surface projection image by projecting voxel values of the volume representation onto a brain surface.

5. The imaging work station according to claim 1, wherein the processor is further programmed to:
    statistically map at least one of the volume representation and the surface projection comparing each voxel with images from a group of subjects with a well-defined status.

6. The imaging work station according to claim 1, wherein the processor is further programmed to:
    receive a magnetic resonance image;
    segment the anatomical feature in the magnetic resonance image; and
    register the segmented anatomical feature to the common space.

7. The imaging work station according to claim 1, further including:
    a display device which displays a representation of the distribution of the radiotracer in the anatomical feature.

8. The imaging work station according to claim 1, wherein the imaging work station receives images from at least one of a positron emission tomography (PET) scanner, and a magnetic resonance (MR) scanner.

9. A method for brain imaging comprising:
    receiving at least one image depicting a distribution of a radiotracer in a region of interest that includes the brain;
    with one or more processors:
        registering the image to a common space defined by a template of the region of interest, the common space including a segmented anatomical feature representing a probability that each voxel is gray matter; and
        extracting a volume representation of the image which depicts the distribution of the radiotracer in the segmented anatomical feature and suppresses the radiotracer outside of the segmented anatomical feature by combining each voxel of the image with the probability of the voxel being gray matter as represented by the registered common space.

10. The method for brain imaging according to claim 9, wherein the radiotracer highlights amyloid deposits.

11. The method for brain imaging according to claim 9, wherein the radiotracer includes at least one of [18F]-Flutemetamol, [18F]-Florbetaben, and [18F]-Florbetapir.

12. The method for brain imaging according to claim 9, further including:
    calculating a surface projection image by projecting voxel values of the volume representation onto a brain surface.

13. The method for brain imaging according to claim 9, further including:
    statistically mapping at least one of the volume representation or the surface projection comparing each voxel with images from a group of subjects with a well-defined status.

14. The method for brain imaging according to claim 9, further including:
    receiving a magnetic resonance image;
    segmenting the magnetic resonance image by the anatomical feature; and
    registering the segmented anatomical feature to the common space.

15. A non-transient computer readable medium carrying software which control one or more processors to perform the method of claim 9.

16. An imaging work station comprising:
one or more processors programmed to:
- receive a positron emission tomography (PET) or single photon emission computed tomography (SPECT) brain image depicting a distribution of a radiotracer in a region of interest of the brain wherein the radiotracer is taken up by both gray matter and white matter;
- register the brain image to a common space defined by a template or an MRI image of the region of interest which includes a segmented anatomical feature that represents probability that each voxel is gray matter; and
- combine each voxel of the registered brain image with the probability of the voxel being gray matter as represented by the segmented anatomical feature of the template or MRI image to extract a volume representation of the brain image which depicts the distribution of the radiotracer in gray matter and suppresses the distribution of the radiotracer in white matter.

\* \* \* \* \*